US008236793B2

(12) United States Patent
Peters et al.

(10) Patent No.: US 8,236,793 B2
(45) Date of Patent: Aug. 7, 2012

(54) DIAZABICYCLIC ARYL DERIVATIVES AS CHOLINERGIC RECEPTOR MODULATORS

(75) Inventors: Dan Peters, Ballerup (DK); Gunnar M. Olsen, Ballerup (DK); Elsebet Østergaard Nielsen, Ballerup (DK); Tino Dyhring Jørgensen, Ballerup (DK); Daniel B Timmermann, Ballerup (DK)

(73) Assignee: Neurosearch A/S, Ballerup (DK)

( * ) Notice: Subject to any disclaimer, the term of this patent is extended or adjusted under 35 U.S.C. 154(b) by 293 days.

(21) Appl. No.: 12/633,505

(22) Filed: Dec. 8, 2009

(65) Prior Publication Data

US 2010/0113428 A1    May 6, 2010

Related U.S. Application Data

(62) Division of application No. 10/586,836, filed as application No. PCT/EP2005/050404 on Feb. 1, 2005, now Pat. No. 7,662,808.

(60) Provisional application No. 60/541,753, filed on Feb. 5, 2004, provisional application No. 60/573,347, filed on May 24, 2004.

(30) Foreign Application Priority Data

Feb. 4, 2004   (DK) ................................. 2004 00171
May 24, 2004  (DK) ................................. 2004 00812

(51) Int. Cl.
*A61K 31/55* (2006.01)
*C07D 243/10* (2006.01)

(52) U.S. Cl. ........................................ 514/221; 540/567
(58) Field of Classification Search .................. None
See application file for complete search history.

(56) References Cited

U.S. PATENT DOCUMENTS

| 5,478,939 | A | 12/1995 | Trybulski et al. |
| 6,407,095 | B1 | 6/2002 | Lochead et al. |
| 6,635,645 | B1 | 10/2003 | Lochead et al. |
| 7,067,507 | B2 | 6/2006 | Pulley et al. |
| 7,223,753 | B2 | 5/2007 | Peters et al. |
| 2002/0086871 | A1 | 7/2002 | O'Neill et al. |
| 2003/0114461 | A1 | 6/2003 | Galli et al. |
| 2003/0153574 | A1 | 8/2003 | Galli et al. |
| 2004/0029884 | A1 | 2/2004 | Gallet et al. |
| 2004/0266757 | A1 | 12/2004 | Galli et al. |
| 2005/0004158 | A1 | 1/2005 | Iyer et al. |
| 2005/0020599 | A1 | 1/2005 | Galli et al. |
| 2009/0181984 | A1* | 7/2009 | Peters et al. .................. 514/256 |
| 2009/0197872 | A1* | 8/2009 | Peters et al. .................. 514/221 |
| 2011/0046118 | A1* | 2/2011 | Peters et al. .................. 514/221 |

FOREIGN PATENT DOCUMENTS

| EP | 1 219 622 A2 | 7/2002 |
| EP | 1219622 | * 7/2002 |
| WO | WO-99/42465 A2 | 8/1999 |
| WO | WO-00/34279 A1 | 6/2000 |
| WO | WO-00/34284 A1 | 6/2000 |
| WO | WO-01/92259 A1 | 12/2001 |
| WO | WO-01/92260 A1 | 12/2001 |
| WO | WO-01/92261 A1 | 12/2001 |
| WO | WO-03/044019 A1 | 5/2003 |
| WO | WO-03/044020 A1 | 5/2003 |
| WO | WO-03/044024 A1 | 5/2003 |
| WO | WO-2004/024729 A1 | 3/2004 |
| WO | WO-2004/029053 A1 | 4/2004 |
| WO | WO-00/44755 A1 | 8/2008 |

OTHER PUBLICATIONS

Cassels. Drug Discovery Today, 2005, 10 (23-24), 1657-1657-65.*
Decker et al. Expert Opinion in Investigational Drugs, 2001, 10(10), 1819-1830.
"Biogenic amines", http://www.nlm.nih.gov/cgi/mesh/2008/MB_cgi?mode=&index=14697&field=all&HM=&II=&PA=&form=&input=, accessed Dec. 12, 2008.
"Receptors Cholinergic", http://www.nlm.nih.gov/cgi/mesh/2008/MB_cgi?mode=&index=11477&field=all&HM=&II=&PA=&form=&input=, accessed Dec. 12, 2008.
"Central Nervous System Diseases", http://www.nlm.nih.gov/cgi/mesh/2008/MB_cgi, accessed Dec. 12, 2008.
Wood et al. Expert Opinion in Investigational Drugs, 2002, 11(4), 457-67.

* cited by examiner

*Primary Examiner* — Noble Jarrell
(74) *Attorney, Agent, or Firm* — Birch Stewart Kolasch & Birch, LLP

(57) ABSTRACT

This invention relates to novel diazabicyclic aryl derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

9 Claims, No Drawings

DIAZABICYCLIC ARYL DERIVATIVES AS CHOLINERGIC RECEPTOR MODULATORS

This application is a divisional application of application Ser. No. 10/586,836, filed Jul. 21, 2006, (U.S. Pat. No. 7,662, 808 B2, issued on Feb. 16, 2010), which is a national phase of PCT application PCT/EP2005/050404 filed on Feb. 1, 2005 and claims priority under 35 U.S.C. 119(e) on U.S. Provisional Application No(s). 60/541,753 and 60/573,347 filed on Feb. 5, 2004 and May 24, 2004; respectively and under 35 U.S.C. 119(a) on Patent Application No(s). PA 2004 00171 and PA 2004 00812 filed in Denmark on Feb. 4, 2004 and May 24, 2004, all of which are hereby incorporated by reference.

TECHNICAL FIELD

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

U.S. Pat. No. 5,478,939 (American Cyanamid) and WO 00/34284 (Sanofi-Synthelabo) both describe 2,5-diazabicyclo[2.2.1]heptane derivatives having affinity for nicotinic receptors.

WO 00/34279, WO 01/92259, WO 01/92260 and WO 01/92261 (Sanofi-Synthelabo), describe 1,4-diazabicyclo[3.3.2]nonane derivatives having affinity for nicotinic receptors.

WO 00/44755 (Abbott) describes diazabicyclic derivatives useful as nicotinic acetylcholine receptor ligands.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic aryl derivatives represented by Formula I

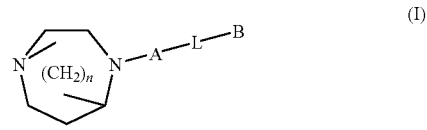

any of its enantiomers or any mixture of its enantiomers, or a pharmaceutically acceptable salt thereof, wherein n is 1, 2 or 3;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group; a 5-6 membered aromatic monocyclic heterocyclic group; or an aromatic bicyclic heterocyclic group; which aromatic groups may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''', —NR'''(C=Z)R'''' and —NR'''(C=Z)NR'''R''''; wherein Z represents O, S or NR''''; wherein R'''' represents hydrogen, alkyl or cyano; R''' represents hydrogen or alkyl; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxyalkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl; and L represents a single (covalent) bond (i.e. L is absent); a linking group selected from —CH$_2$—, —CH$_2$—CH$_2$—, —CH=CH—, —C≡C—, —Y—(CH$_2$)$_m$—, —(CH$_2$)$_m$—Y—, —CONR''''—, —NR''''CO—, —NR''''CONR''''—, —(SO$_2$)NR''''— and —NR''''(SO$_2$)—; wherein R'''' represents hydrogen or alkyl; Y represents —O—, —S—, —S—CH$_2$—, —SO—, —SO$_2$—, —NR''''''—; wherein R'''''' represents hydrogen or alkyl; and m is 0, 1, 2 or 3.

In its second aspect the invention provides pharmaceutical compositions comprising a therapeutically effective amount of the diazabicyclic aryl derivative of the invention, or a pharmaceutically-acceptable addition salt thereof, together with at least one pharmaceutically-acceptable carrier or diluent.

In a further aspect the invention relates to the use of the diazabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicyclic aryl derivative of the invention.

Other objects of the invention will be apparent to the person skilled in the art from the following detailed description and examples.

DETAILED DISCLOSURE OF THE INVENTION

Diazabicyclic Aryl Derivative

In a first aspect novel diazabicyclic aryl derivatives are provided. The diazabicyclic aryl derivatives of the invention may be represented by the general Formula I

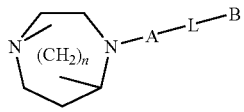

(I)

any of its enantiomers or any mixture of its enantiomers, or a pharmaceutically acceptable salt thereof, wherein n is 1, 2 or 3;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group; a 5-6 membered aromatic monocyclic heterocyclic group; or an aromatic bicyclic heterocyclic group; which aromatic groups may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR''''R'''', —NR'''(C═Z)R'''' and —NR'''(C═Z)NR'''R''''; wherein Z represents O, S or NR''''''; wherein R'''''' represents hydrogen, alkyl or cyano; R''' represents hydrogen or alkyl; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxyalkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl; and L represents a single (covalent) bond (i.e. L is absent); a linking group selected from —CH$_2$—, —CH$_2$—CH$_2$—, —CH═CH—, —C≡C—, —Y—(CH$_2$)$_m$—, —(CH$_2$)$_m$—Y—, —CONR''''''—, —NR''''''CO—, —NR''''''CONR''''''—, —(SO$_2$)NR''''''— and —NR''''''(SO$_2$)—; wherein R'''''' represents hydrogen or alkyl; Y represents —O—, —S—, —S—CH$_2$—, —SO—, —SO$_2$—, —NR''''''—; wherein R'''''' represents hydrogen or alkyl; and m is 0, 1, 2 or 3.

In a preferred embodiment the diazabicyclic aryl derivative is a compound of Formula I wherein n is 1, 2 or 3. In a more preferred embodiment n is 1 or 2. In an even more preferred embodiment n is 2.

In a second embodiment the diazabicyclic aryl derivative is a compound of Formula I wherein A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In one preferred embodiment A represents a phenyl group; or a 5-membered aromatic monocyclic heterocyclic group selected from furanyl, thienyl, pyrrolyl, oxazolyl, thiazolyl, imidazolyl, pyrazolyl, isoxazolyl, isothiazolyl, oxadiazolyl, triazolyl and thiadiazolyl; or a 6-membered aromatic monocyclic heterocyclic group selected from pyridyl, pyridazinyl, pyrimidinyl, pyrazinyl and triazinyl; or a aromatic bicyclic heterocyclic group selected from indolyl, benzo[b]furanyl, benzo[b]thienyl, and benzothiazolyl.

In another preferred embodiment A represents a phenyl group; or a 5-membered aromatic monocycle heterocyclic group selected from

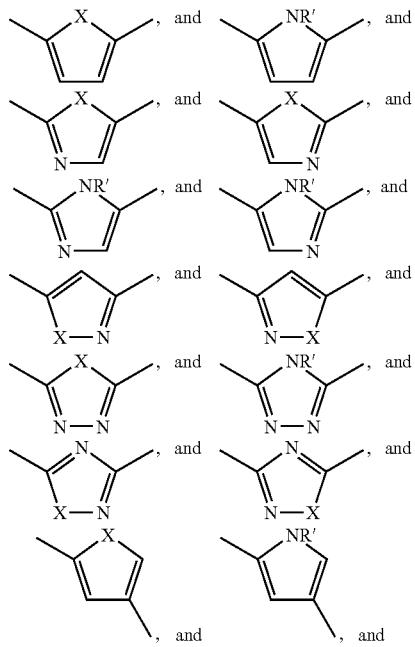

-continued

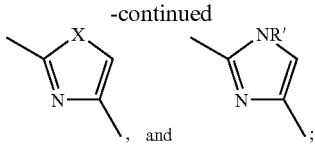

wherein X represents O, S or Se; and R' represents hydrogen or alkyl; or a 6-membered aromatic monocyclic heterocyclic group selected from

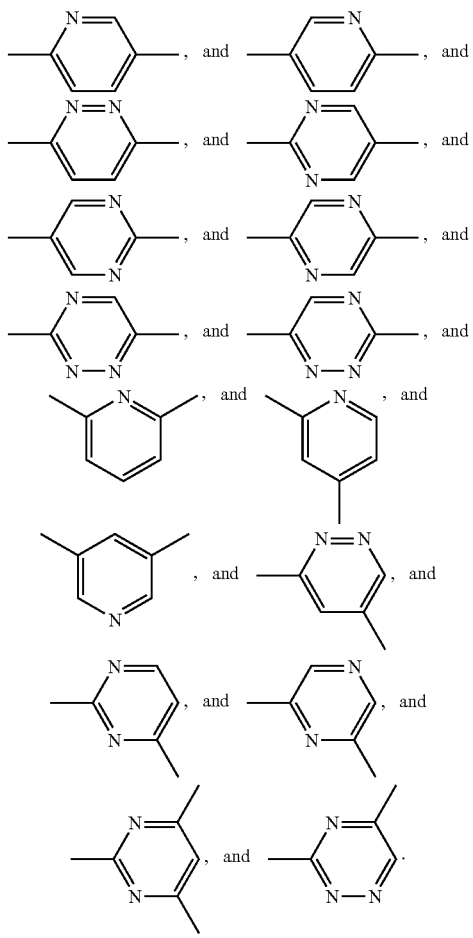

In a third preferred embodiment A represents a phenyl group; or a 5-membered aromatic monocyclic heterocyclic group selected from

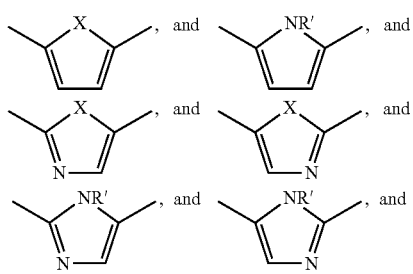

-continued

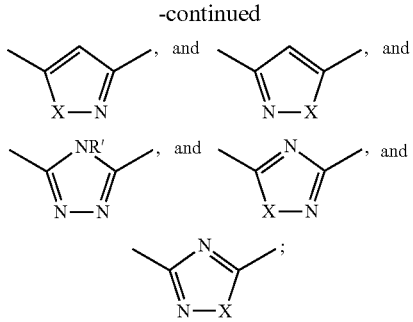

wherein X represents O, S or Se; and R' represents hydrogen or alkyl; or a 6-membered aromatic monocyclic carbocyclic or heterocyclic group selected from

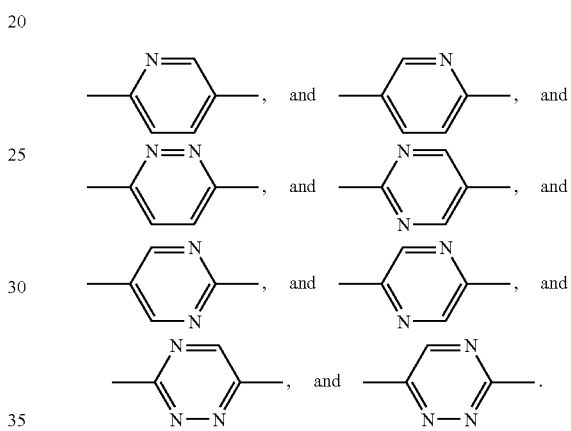

In a most preferred embodiment A represents a phenyl group.

In a fourth preferred embodiment A represents a 5-membered aromatic monocyclic heterocyclic group selected from

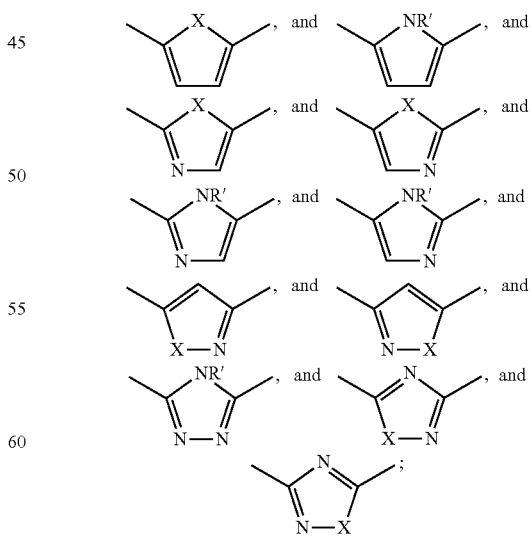

wherein X represents O, S or Se; and R' represents hydrogen or alkyl.

In a fifth preferred embodiment A represents a 5-membered aromatic monocyclic heterocyclic group selected from

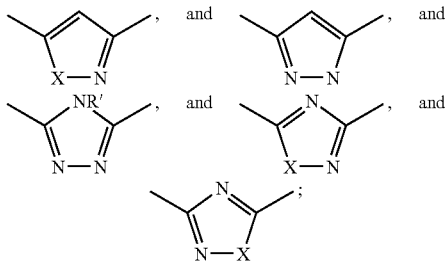

wherein X represents O, S or Se; and R' represents hydrogen or alkyl.

In a sixth preferred embodiment A represents

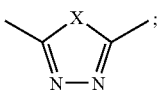

wherein X represents O, S or Se.

In a most preferred embodiment A represents a thiadiazolyl group.

In a seventh preferred embodiment A represents a 5-membered aromatic monocyclic heterocyclic group selected from

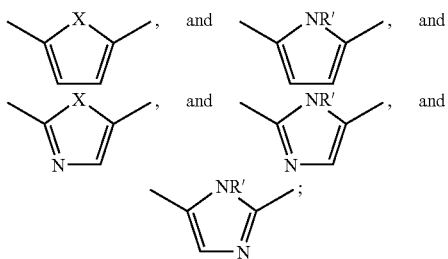

wherein X represents O, S or Se; and R' represents hydrogen or alkyl.

In an eighth preferred embodiment A represents a 6-membered aromatic monocyclic heterocyclic group selected from

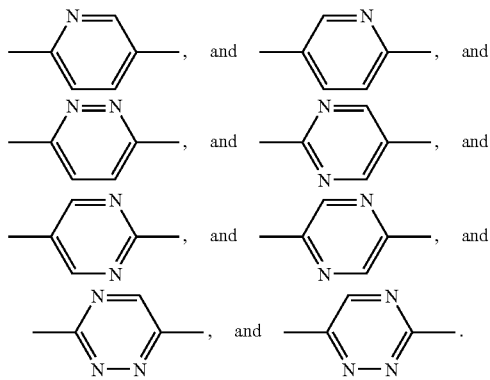

In a ninth preferred embodiment A represents a 6-membered aromatic monocyclic heterocyclic group selected from

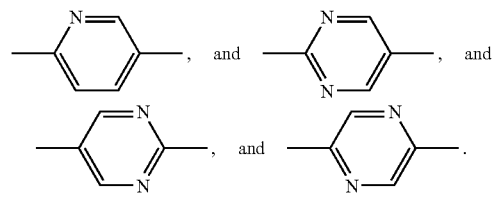

In a tenth preferred embodiment A represents a phenyl group; or a 5-membered aromatic monocyclic heterocyclic group selected from furanyl, thienyl, pyrrolyl, oxazolyl, thiazolyl, imidazolyl, pyrazolyl, isoxazolyl, isothiazolyl, oxadiazolyl, triazolyl and thiadiazolyl; or a 6-membered aromatic monocyclic heterocyclic group selected from pyridyl, pyridazinyl, pyrimidinyl, pyrazinyl and triazinyl.

In a most preferred embodiment A represents a phenyl, a thiadiazolyl, a pyridyl or pyridazinyl group.

In a second embodiment the diazabicyclic aryl derivative is a compound of Formula I wherein B represents a phenyl, naphthyl group, a 5-6 membered aromatic monocyclic heterocyclic group, or an aromatic bicyclic heterocyclic group, which aromatic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR""R"", —NR'"(C=Z)R"" and —NR'"(C=Z)NR'"R""; wherein Z represents O, S or NR""'; wherein R""' represents hydrogen, alkyl or cyano; and R'" represents hydrogen or alkyl; and R"" represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl.

In more preferred embodiment B represents a phenyl or naphthyl group, which aromatic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR""R"", —NR'"(C=Z)R"" and —NR'"(C=Z)NR'"R""; wherein Z represents O, S or NR""'; wherein R""' represents hydrogen, alkyl or cyano; and R'" represents hydrogen or alkyl; and R"" represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl; or B represents a 5-6 membered aromatic monocyclic heterocyclic group, which aromatic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'"R"", —NR'"(C=Z)R"" and —NR'"(C=Z)NR'"R""; wherein Z represents O, S or NR""'; R""' represents hydrogen, alkyl or cyano; and R'" represents hydrogen or alkyl; and R"" represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxyalkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl; or B represents an aromatic bicyclic heterocyclic group, which bicyclic heterocyclic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''', —NR'''(C=Z)R'''' and —NR'''(C=Z)NR'''R''''; wherein Z represents O, S or NR''''; wherein R'''' represents hydrogen, alkyl or cyano; and R''' represents hydrogen or alkyl; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxyalkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl.

In a third preferred embodiment B represents a phenyl or naphthyl group, which aromatic group may optionally be substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR''''R'''' and —NR'''(C=Z)NR'''R''''; wherein Z represents O, S or NH; R''' represents hydrogen, alkyl or cyano; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl.

In a fourth preferred embodiment B represents a phenyl or naphthyl group, optionally substituted one or two times with alkyl, cycloalkyl, cycloalkyl-alkyl, hydroxy, alkoxy, cyanoalkyl, halo, trihaloalkyl, trihaloalkoxy, cyano, amino and/or nitro.

In a fifth preferred embodiment B represents a phenyl or naphthyl group.

In a sixth preferred embodiment B represents a phenyl or naphthyl group, optionally substituted with —CONR''''R'''' or —NR'''(CO)NR'''R''''; wherein R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, trihaloalkoxy, amino, nitro, carbamoyl and/or amido; or furanyl, oxazolyl, isoxazolyl, thiazolyl, isothiazolyl, thiadiazolyl, imidazolyl, pyrazolyl, pyridinyl, pyrimidinyl or pyridazinyl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In a more preferred embodiment R''' represents hydrogen or alkyl; and R'''' represents furan-3-yl, oxazol-2-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, pyridin-4-yl, pyrimidin-2-yl, pyrimidin-4-yl or pyridazin-3-yl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In a seventh preferred embodiment B represents a phenyl or naphthyl group, substituted with —NR'''(CO)NR'''R''''; wherein R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, carbamoyl and/or amido; or furan-3-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, or pyridin-4-yl, which heterocyclic group may optionally be substituted with alkyl, hydroxy-alkyl, cycloalkyl, hydroxy, alkoxy, alkoxy-alkyl, halo, trihaloalkyl, cyano or phenyl.

In an eight preferred embodiment B represents a 5-6 membered aromatic monocyclic heterocyclic group, which aromatic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''' and —NR'''(C=Z)NR'''R''''; wherein Z represents O, S or NH; R''' represents hydrogen, alkyl or cyano; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl.

In a more preferred embodiment B represents a furanyl, thienyl, pyrrolyl, oxazolyl, isoxazolyl, thiazolyl, isothiazolyl, thiadiazolyl, imidazolyl, pyrazolyl, pyridinyl, pyrimidinyl or pyridazinyl group, which heterocyclic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''' and —NR'''(C=Z)NR'''R''''; wherein Z represents O, S or NH; R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, trihaloalkoxy, amino, nitro, carbamoyl and/or amido; or furanyl, oxazolyl, isoxazolyl, thiazolyl, isothiazolyl, thiadiazolyl, imidazolyl, pyrazolyl, pyridinyl, pyrimidinyl or pyridazinyl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In an even more preferred embodiment R''' represents hydrogen or alkyl; and R'''' represents furan-3-yl, oxazol-2-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, pyridin-4-yl, pyrimidin-2-yl, pyrimidin-4-yl or pyridazin-3-yl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In a ninth preferred embodiment B represents a furan-2-yl, furan-3-yl, thien-2-yl, thien-3-yl, pyrrol-2-yl, oxazol-2-yl, isoxazol-3-yl, thiazol-2-yl, isothiazol-3-yl, 1,3,4-thiadiazol-2-yl, imidazol-2-yl, pyrazol-3-yl, pyridin-3-yl, pyrimidin-2-yl or pyridazin-3-yl group, which aromatic group may optionally substituted with —NR'''(CO)NR'''R''''; wherein R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, carbamoyl and/or amido; or furan-3-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, or pyridin-4-yl, which heterocyclic group may optionally be substituted with alkyl, hydroxy-alkyl, cycloalkyl, hydroxy, alkoxy, alkoxy-alkyl, halo, trihaloalkyl, cyano or phenyl.

In a tenth preferred embodiment B represents an aromatic bicyclic heterocyclic group, which bicyclic heterocyclic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''' and —NR'''(C=Z)NR'''R''''; wherein Z represents O, S or NH; R''' represents hydrogen, alkyl or cyano; and R'''' represents hydrogen, alkyl, alkenyl, alkynyl, cycloalkyl, cycloalkenyl, or a monocyclic carbocyclic or heterocyclic group, optionally substituted one or more times with substituents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, amido, sulfamoyl, phenyl or benzyl.

In an eleventh preferred embodiment B represents indolyl, in particular indol-2-, 5-or 6-yl; benzo[b]furanyl, in particular benzofuran-2-, 5-or 6-yl; benzo[b]thienyl, in particular benzothien-2-, 5-or 6-yl; or benzothiazolyl, in particular benzothiazol-2-, 5-or 6-yl; which bicyclic heterocyclic group may optionally be substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, —CONR'''R'''' and —NR'''(C=Z)NR'''R''''; wherein Z represents O, S or NH; R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, trihaloalkoxy, amino, nitro, carbamoyl and/or amido; or furanyl, oxazolyl, isoxazolyl, thiazolyl, isothiazolyl, thiadiazolyl, imidazolyl, pyrazolyl, pyridinyl, pyrimidinyl or pyridazinyl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In a more preferred embodiment R''' represents hydrogen or alkyl; and R'''' represents —CH$_3$, —CH=CH$_2$, —CH=CH—CH=CH$_2$, cyclopenta-1-enyl or cyclopenta-2,4-dienyl; furan-3-yl, oxazol-2-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, pyrimidin-2-yl, pyrimidin-4-yl or pyridazin-3-yl, which heterocyclic group may optionally be substituted with alkyl, hydroxy-alkyl, cycloalkyl, cycloalkyl-alkyl, hydroxy, alkoxy, alkoxy-alkyl, cyanoalkyl, halo, trihaloalkyl, trihaloalkoxy, cyano, amino, nitro or phenyl.

In a twelfth preferred embodiment B represents indol-2-, 5-or 6-yl; benzofuran-2-, 5-or ±6-yl; benzothien-2-, 5-or 6-yl; or benzothiazol-2-, 5-or 6-yl; which bicyclic heterocyclic group is substituted with —NR'''(CO)NR'''R''''; wherein R''' represents hydrogen or alkyl; and R'''' represents alkyl, alkenyl, cycloalkyl, cycloalkenyl, or cycloalkenyl substituted two times with oxo; or phenyl or benzyl, which phenyl and benzyl may optionally be substituted one to three times with alkyl, hydroxy, alkoxy, halo, trihaloalkyl, carbamoyl and/or amido; or furan-3-yl, isoxazol-3-yl, isoxazol-5-yl, 1,3-thiazol-2-yl, 1,3-thiazol-5-yl, isothiazolyl, 1,3,4-thiadiazol-2-yl, 1,2,4-thiadiazol-5-yl, imidazol-2-yl, pyrazol-1-yl, pyridin-3-yl, or pyridin-4-yl, which heterocyclic group may optionally be substituted with alkyl, hydroxy-alkyl, cycloalkyl, hydroxy, alkoxy, alkoxy-alkyl, halo, trihaloalkyl, trihaloalkoxy, cyano or phenyl.

In a thirteenth preferred embodiment B represents a 5-membered aromatic monocyclic heterocyclic group selected from

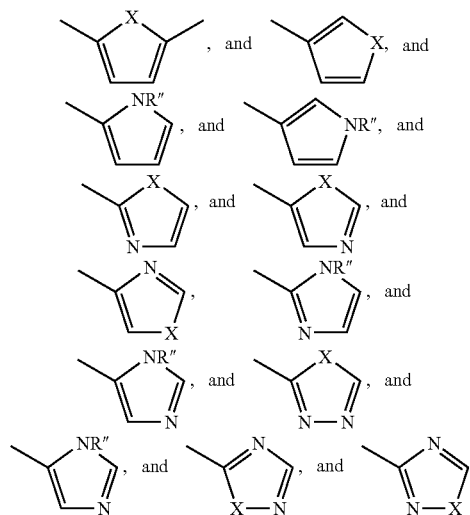

wherein X represents O, S or Se; and R'' represents hydrogen or alkyl; which 5-membered aromatic monocyclic heterocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In a fourteenth preferred embodiment B represents a 5-membered aromatic monocyclic heterocyclic group selected from

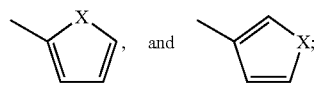

wherein X represents O or S; which 5-membered aromatic monocyclic heterocyclic group is optionally substituted one or more times with substituents selected from the group consisting of alkyl, hydroxy, alkoxy, halo, trihaloalkyl, trihaloalkoxy, cyano and nitro.

In a fifteenth preferred embodiment B represents a 6-membered aromatic monocyclic heterocyclic group selected from

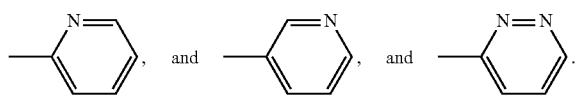

In a seventeenth preferred embodiment B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R''''; wherein R'''' represents hydrogen, alkyl or cycloalkyl.

In an eighteenth preferred embodiment B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In a nineteenth preferred embodiment B represents a phenyl group or a pyridyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In a fourth embodiment the diazabicyclic aryl derivative is a compound of Formula I wherein n is 2; A represents a 5-membered aromatic monocyclic heterocyclic group of formula

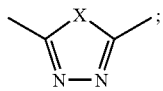

wherein X represents O, S or Se; or a 6-membered aromatic monocyclic heterocyclic group selected from

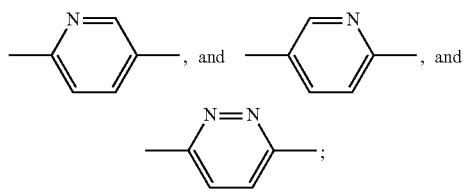

and

B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)R''''; wherein R'''' represents hydrogen, alkyl or cycloalkyl.

In a sixth embodiment the diazabicyclic aryl derivative is a compound of Formula I wherein n is 2; A represents a 5-membered aromatic monocyclic heterocyclic group of formula

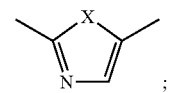

wherein X represents O, S or Se; or a 6-membered aromatic monocyclic heterocyclic group selected from

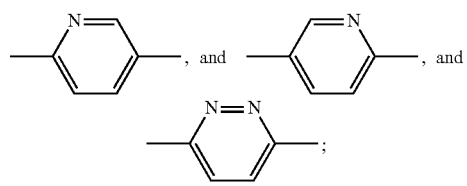

and

B represents a phenyl or naphthyl group, optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro; or a 5-membered aromatic monocyclic heterocyclic group selected from

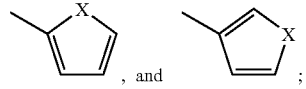

wherein X represents O, S or Se; which 5-membered aromatic monocyclic heterocyclic group is optionally substituted one or more times with substituents selected from the group consisting of alkyl, hydroxy, alkoxy, halo, trihaloalkyl, trihaloalkoxy, cyano and nitro; or a 6-membered aromatic monocyclic heterocyclic group selected from

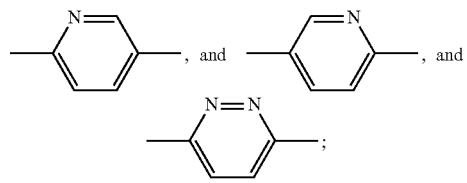

which 6-membered aromatic monocyclic heterocyclic group is optionally substituted substituted one or more times with substituents selected from the group consisting of alkyl, hydroxy, alkoxy, halo, trihaloalkyl, trihaloalkoxy, cyano and nitro.

In a seventh embodiment the diazabicyclic aryl derivative is a compound of Formula I wherein L represents a single (covalent) bond (i.e. L is absent); a linking group selected from —$CH_2$—, —$CH_2$—$CH_2$—, —CH=CH—, —C≡C—, —Y—$(CH_2)_m$—, —$(CH_2)_m$—Y—, —CONR''''—, —NR''''CO—, —NR''''CONR''''—, —$(SO_2)$NR''''— and —NR''''$(SO_2)$—; wherein R'''' represents hydrogen or alkyl; Y represents —O—, —S—, —S—CH₂—, —SO—, —SO₂—, —NR""''—; wherein R"""' represents hydrogen or alkyl; and m is 0, 1, 2 or 3.

In a more preferred embodiment L represents —O—, —S—, —S—CH₂—, —CH₂—S—, —SO—, —SO₂—, —NR""''—, —CH₂—, —CH₂—CH₂—, —CH=CH—, —C≡C—, —NR""''CO—, —NR""''CONR""''— or —NR""''(SO₂)—; wherein R""'' represents hydrogen or alkyl.

In an even more preferred embodiment L represents —O—, —S—, —S—CH₂—, —CH₂—S—, —SO—, —SO₂—, —NR""''—, —CH=CH—, —C≡C—, —NR""''CO— or —NR""''CONR""''—; wherein R""'' represents hydrogen or alkyl.

In a still more preferred embodiment L represents —O—, —S—, —S—CH₂—, —SO—, —C≡C—, —NHCO—, —NHCONH— or NH(SO₂)—.

In a most preferred embodiment L represents —O—, —S—, —S—CH₂—, —SO—, —C≡C—, —NHCO— or —NHCONH—.

In an eighth embodiment the diazabicyclic aryl derivative is a compound of Formula I wherein n is 2; A represents phenyl, thiadiazolyl, pyridyl or pyridazinyl; B represents a phenyl or pyridyl group, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH₂—, —SO—, —C≡C—, —NHCO—, —NHCONH— or —NH(SO₂)—.

In a ninth embodiment the diazabicyclic aryl derivative is a compound of Formula I wherein n is 2; A represents phenyl; B represents a phenyl or naphthyl group, optionally substituted one or two times with alkyl, cycloalkyl, cycloalkylalkyl, hydroxy, alkoxy, cyanoalkyl, halo, trihaloalkyl, trihaloalkoxy, cyano, amino and/or nitro; and L represents —O—, —S—, —S—CH₂—, —CH₂—S—, —SO—, —SO₂—, —NR""''—, —CH₂—, —CH₂—CH₂—, —CH=CH—, —C≡C—, —NR""''CO— or —NR""''CONR""''—; wherein R""'' represents hydrogen or alkyl.

In a more preferred embodiment n is 2; A represents phenyl; B represents a phenyl or naphthyl group; and L represents —NR""''CO— or —NR""''CONR""''—; wherein R""'' represents hydrogen or alkyl.

In an even more preferred embodiment n is 2; A represents phenyl; B represents a phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH₂—, —SO—, —C≡C—, —NHCO—, —NHCONH— or —NH(SO₂)—.

In a most preferred embodiment the diazabicyclic aryl derivative of the invention is
N-[4-(1,4-Diaza-bicyclo[3.2.2]non-4-yl)-phenyl]-benzamide;
1-[4-(1,4-Diaza-bicyclo[3.2.2]non-4-yl)-phenyl]-3-phenyl-urea;
N-[4-(1,4-Diaza-bicyclo[3.2.2]non-4-yl)-phenyl]-2-nitro-benzamide;
N-[4-(1,4-Diaza-bicyclo[3.2.2]non-4-yl)-phenyl]-3-nitro-benzamide;
N-[4-(1,4-Diaza-bicyclo[3.2.2]non-4-yl)-phenyl]-4-nitro-benzamide;
2-Amino-N-[4-(1,4-diaza-bicyclo[3.2.2]non-4-yl)-phenyl]-benzamide;
3-Amino-N-[4-(1,4-diaza-bicyclo[3.2.2]non-4-yl)-phenyl]-benzamide;
4-Amino —N-[4-(1,4-diaza-bicyclo[3.2.2]non-4-yl)-phenyl]-benzamide;
2-Acetylamino-N-[4-(1,4-diaza-bicyclo[3.2.2]non-4-yl)-phenyl]-benzamide;
3-Acetylamino-N-[4-(1,4-diaza-bicyclo[3.2.2]non-4-yl)-phenyl]-benzamide;
4-Acetylamino-N-[4-(1,4-diaza-bicyclo[3.2.2]non-4-yl)-phenyl]-benzamide;
N-[4-(1,4-Diaza-bicyclo[3.2.2]non-4-yl)-phenyl]-3-methoxy-benzamide;
N-[4-(1,4-Diaza-bicyclo[3.2.2]non-4-yl)-phenyl]-benzenesulfonamide;
N-[4-(1,4-Diaza-bicyclo[3.2.2]non-4-yl)-phenyl]-4-methoxy-benzamide;
N-[4-(1,4-Diaza-bicyclo[3.2.2]non-4-yl)-phenyl]-3-cyano-benzamide;
N-[4-(1,4-Diaza-bicyclo[3.2.2]non-4-yl)-phenyl]-4-cyano-benzamide;
N-[4-(1,4-Diaza-bicyclo[3.2.2]non-4-yl)-phenyl]-3-fluoro-benzamide;
N-[4-(1,4-Diaza-bicyclo[3.2.2]non-4-yl)-phenyl]-4-fluoro-benzamide;
N-[4-(1,4-Diaza-bicyclo[3.2.2]non-4-yl)-phenyl]-2-fluoro-benzamide;
N-[4-(1,4-Diaza-bicyclo[3.2.2]non-4-yl)-phenyl]-4-nitro-benzenesulfonamide; or
4-Amino —N-[4-(1,4-diaza-bicyclo[3.2.2]non-4-yl)-phenyl]-benzenesulfonamide;

or an enantiomers or a mixture of its enantiomers, or a pharmaceutically acceptable salt thereof.

In a tenth embodiment the diazabicyclic aryl derivative is a compound of Formula I wherein n is 2; A represents a 5-membered aromatic monocyclic heterocyclic group selected from

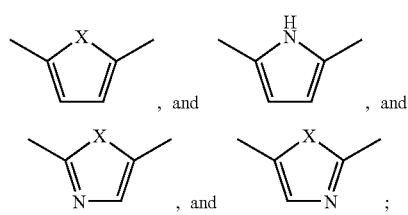

wherein X represents O, S or Se; or a 6-membered aromatic monocyclic carbocyclic or heterocyclic group selected from

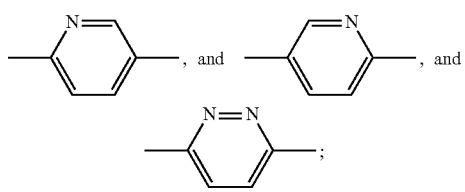

and

B represents a phenyl or naphthyl group, optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro; or a 6-membered aromatic monocyclic heterocyclic group selected from

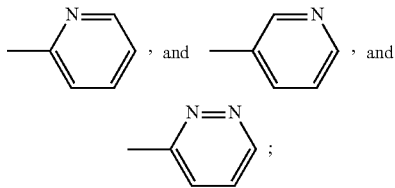

and

L represents a linking group selected from —O—, —S—, —S—CH₂—, —CH₂—S—, —SO—, —SO₂—, —NR''''—, —CH₂—, —CH₂—CH₂—, —CH=CH—, —C≡C—, —NR''''—CO— or —NR''''—CO—NR''''—; wherein R'''' represents hydrogen or alkyl.

In an eleventh embodiment the diazabicyclic aryl derivative is a compound of Formula I wherein n is 2; A represents a group of formula

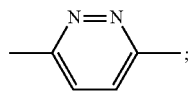

and

B represents phenyl or a group of formula

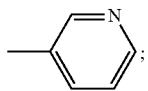

which phenyl or heteroaryl is optionally substituted with halo, alkoxy or amino; and L represents —O—, —S—, —S—CH₂—, —SO—, —C≡C—, —NH—CO— or —NH—CO—NH—.

In a twelfth eleventh embodiment the diazabicyclic aryl derivative is a compound of Formula I wherein n is 2; A represents thiadiazolyl, pyridyl or pyridazinyl; B represents phenyl or pyridyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH₂—, —SO—, —C≡C—,—NHCO—, —NHCONH— or —NH(SO₂)—.

In a more preferred embodiment n is 2; A represents thiadiazolyl; B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH₂—, —SO—, —C≡C—,—NHCO—, —NHCONH— or NH(SO₂)—.

In a thirteenth embodiment the diazabicyclic aryl derivative is a compound of Formula I wherein n is 2; A represents a group of formula

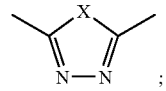

wherein

X represents O, S or Se; B represents phenyl, optionally substituted one or two times with halo, trihaloalkyl, trihaloalkoxy, cyano, amino and/or nitro; and L represents —O—, —S—, —S—CH₂—, —SO—, —C≡C—,—NR''''CO— or —NR''''—CO—NR''''—; wherein R'''' represents hydrogen or alkyl.

In a preferred embodiment A represents thiadiazolyl.

In another preferred embodiment B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl.

In a third preferred embodiment L represents —O—, —S—, —S—CH₂—, —SO—, —C≡C—, —NHCO—, —NHCONH— or NH(SO₂)—.

In a most preferred embodiment the diazabicyclic aryl derivative of the invention is 4-(5-Benzylsulfanyl-[1.3.4]-thiadiazol-3-yl)-1,4-diazabicyclo[3.2.2]nonane;

or an enantiomers or a mixture of its enantiomers, or a pharmaceutically acceptable salt thereof.

In yet another preferred embodiment A represents pyridyl or pyridazinyl.

In a most preferred embodiment the diazabicyclic aryl derivative of the invention is 4-(6-Phenylethynyl-pyridazin-3-yl)-1,4-diaza-bicyclo [3.2.2]nonane;

4-[6-(4-Amino-phenylethynyl)-pyridazin-3-yl]-1,4-diaza-bicyclo[3.2.2]nonane;

4-[6-(3-Fluoro-phenylethynyl)-pyridazin-3-yl]-1,4-diazabicyclo[3.2.2]nonane;

4-[6-(4-Methoxy-phenylethynyl)-pyridazin-3-yl]-1,4-diaza-bicyclo[3.2.2]nonane;

4-[6-(3-Pyridinylethynyl)-pyridazin-3-yl]-1,4-diaza-bicyclo[3.2.2]nonane;

4-(6-Phenylsulfanyl-pyridazin-3-yl)-1,4-diaza-bicyclo [3.2.2]nonane;

4-(6-Phenylsulfinyl-pyridazin-3-yl)-1,4-diaza-bicyclo [3.2.2]nonane;

4-(6-Phenoxy-pyridazin-3-yl)-1,4-diaza-bicyclo[3.2.2] nonane;

1-[6-(1,4-Diaza-bicyclo[3.2.2]non-4-yl)-pyridin-3-yl]-3-(2-nitro-phenyl)-urea-1-N-oxide;

N-[6-(1,4-Diaza-bicyclo[3.2.2]non-4-yl)-pyridin-3-yl]-benzamide;

1-[6-(1,4-Diaza-bicyclo[3.2.2]non-4-yl)-pyridin-3-yl]-3-phenyl-urea;

N-[6-(1,4-Diaza-bicyclo[3.2.2]non-4-yl)-pyridin-3-yl]-4-nitro-benzamide;

N-[6-(1,4-Diaza-bicyclo[3.2.2]non-4-yl)-pyridin-3-yl]-3-nitro-benzamide;

4-Amino—N-[6-(1,4-diaza-bicyclo[3.2.2]non-4-yl)-pyridin-3-yl]-benzamide;

3-Amino-N-[6-(1,4-diaza-bicyclo[3.2.2]non-4-yl)-pyridin-3-yl]-benzamide;

4-Acetylamino-N-[6-(1,4-diaza-bicyclo[3.2.2]non-4-yl)-pyridin-3-yl]-benzamide;

3-Acetylamino-N-[6-(1,4-diaza-bicyclo[3.2.2]non-4-yl)-pyridin-3-yl]-benzamide;

N-[6-(1,4-Diaza-bicyclo[3.2.2]non-4-yl)-pyridin-3-yl]-3-methoxy-benzamide;

N-[6-(1,4-Diaza-bicyclo[3.2.2]non-4-yl)-pyridin-3-yl]-3-cyano-benzamide; or

N-[6-(1,4-Diaza-bicyclo[3.2.2]non-4-yl)-pyridin-3-yl]-4-cyano-benzamide;

or an enantiomers or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention a 5-6 membered aromatic monocyclic heterocyclic designates a 5-6 membered heteroaryl, which holds one or more heteroatoms in its ring structure. Preferred heteroatoms include nitrogen (N), oxygen (O), and sulphur (S).

Preferred 5-6 membered heteroaryl groups of the invention include furanyl, in particular furan-2-or 3-yl; thienyl, in particular thien-2-or 3-yl; selenophenyl, in particular selenophen-2-or 3-yl; pyrrolyl (azolyl), in particular pyrrol-2-or 3-yl; oxazolyl, in particular oxazol-2,4-or 5-yl; thiazolyl, in particular thiazol-2,4-or 5-yl; imidazolyl, in particular imidazol-2-or 4-yl; pyrazolyl, in particular pyrazol-3-or 4-yl; isoxazolyl, in particular isoxazol-3,4-or 5-yl; isothiazolyl, in particular isothiazol-3-, 4-or 5-yl; oxadiazolyl, in particular 1,2,3-oxadiazol-4-or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4-or 5-yl, or 1,3,4-thiadiazol-2-yl; pyridyl, in particular pyrid-2-, 3-or 4-yl; pyridazinyl, in particular pyridazin-3-or 4-yl; pyrimidinyl, in particular pyrimidin-2-, 4-or 5-yl; pyrazinyl, in particular pyrazin-2-or 3-yl; and triazinyl, in particular 1,2,4-or 1,3,5-triazinyl.

More preferred 5 membered heteroaryl groups of the invention include furanyl, in particular furan-2-or 3-yl; thienyl, in particular thien-2-or 3-yl; pyrrolyl (azolyl), in particular pyrrol-2-or 3-yl; oxazolyl, in particular oxazol-2,4-or 5-yl; thiazolyl, in particular thiazol-2,4-or 5-yl; isoxazolyl, in particular isoxazol-3,4-or 5-yl; isothiazolyl, in particular isothiazol-3-, 4-or 5-yl; and thiadiazolyl, in particular 1,2,3-thiadiazol-4-or 5-yl, or 1,3,4-thiadiazol-2-yl.

Most preferred 5 membered heteroaryl groups of the invention include furanyl, in particular furan-2-or 3-yl; and thienyl, in particular thien-2-or 3-yl.

More preferred 6 membered heteroaryl groups of the invention include pyridyl, in particular pyrid-2-, 3-or 4-yl; and pyrazinyl, in particular pyrazin-2-or 3-yl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five-and six-membered heterocyclic rings containing one or more heteroatoms. Preferred heteroatoms include nitrogen (N), oxygen (O), and sulphur (S).

Preferred bicyclic heteroaryl groups of the invention include indolizinyl, in particular indolizin-2-, 5-or 6-yl; indolyl, in particular indol-2-, 5-or 6-yl; isoindolyl, in particular isoindol-2-, 5-or 6-yl; benzo[b]furanyl, in particular benzofuran-2-, 5-or 6-yl; benzo[b]thienyl, in particular benzothien-2-, 5-or 6-yl; benzoimidazolyl, in particular benzoimidazol-2-, 5-or 6-yl; benzothiazolyl, in particular benzothiazol-2-, 5-or 6-yl; purinyl, in particular purin-2-or 8-yl; quinolinyl, in particular quinolin-2-, 3-, 6-or 7-yl; isoquinolinyl, in particular isoquinolin-3-, 6-or 7-yl; cinnolinyl, in particular cinnolin-6-or 7-yl; phthalazinyl, in particular phthalazin-6-or 7-yl; quinazolinyl, in particular quinazolin-2-, 6-or 7-yl; quinoxalinyl, in particular quinoxalin-2-or 6-yl; 1,8-naphthyridinyl, in particular 1,8-naphthyridin-2-, 3-, 6-or 7-yl; and pteridinyl, in particular pteridin-2-, 6-or 7-yl.

More preferred bicyclic heteroaryl groups of the invention include indolyl, in particular indol-2-, 5-or 6-yl; benzo[b]furanyl, in particular benzofuran-2-, 5-or 6-yl; benzo[b]thienyl, in particular benzothien-2-, 5-or 6-yl; benzoimidazolyl, in particular benzoimidazol-2-, 5-or 6-yl; benzothiazolyl, in particular benzothiazol-2-, 5-or 6-yl; and quinoxalinyl, in particular quinoxalin-2-or 6-yl.

Most preferred bicyclic heteroaryl groups of the invention include indolyl, in particular indol-2-, 5-or 6-yl; benzo[b]furanyl, in particular benzofuran-2-, 5-or 6-yl; benzo[b]thienyl, in particular benzothien-2-, 5-or 6-yl; and benzothiazolyl, in particular benzothiazol-2-, 5-or 6-yl.

Pharmaceutically Acceptable Salts

The diazabicyclic aryl derivative of the invention may be provided in any form suitable for the intended administration. Suitable forms include pharmaceutically (i.e. physiologically) acceptable salts, and pre-or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Particularly preferred onium salts of the invention include those created at the N' position according to the following formula I'

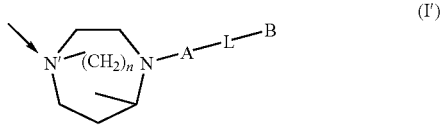

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d-or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an diazabicyclic aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with drawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

1,4-Diazabicyclo[3.2.2]nonane (Intermediate Compound)

The title compound was prepared according to *J. Med. Chem.* 1993 36 2311-2320 (and according to a slightly modified method below).

1,4-Diazabicyclo[3.2.2]nonane (Intermediate Compound)

To the solution of 1,4-diazabicyclo[3.2.2]nonan-3-one (15.8 g; 113 mmol) in absolute dioxane (130 ml) LiAlH$_4$ (4.9 g; 130 mmol) was added under argon. The mixture was refluxed for 6 h and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate Compound)

To the solution of 3-quinuclidinone hydrochloride (45 g; 278 mmol) in 90 ml of water hydroxylamine hydrochloride (21 g; 302 mmol) and sodium acetate (CH$_3$COOH×3H$_2$O; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid* (190 g). The temperature of the solution during the reaction was kept at 130° C. After addition of all oxime the solution was stirred for 20 minutes at the same temperature, then transferred to an enamelled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

The filtrate was evaporated and the residue was chromatographed on a silica gel (Merck, 9385, 230-400 mesh) column with acetone as eluent. The solvent was evaporated and the residue recrystallized from ethyl etanoate to yield 1,3-diazabicyclo[3.2.2]nonan-4-one (10.2 g; 26%) as colourless fine crystals with mp. 125-126° C.

Polyphosphoric Acid*

85% Orthophosphoric acid (500 g; 294 ml; 4.337 mol) was placed into 2000 ml flask and then phosphor pentoxide (750 g; 5.284 mol) was added at room temperature (ratio acid-pentoxide, 2:3). The mixture was stirred at 200-220° C. for 2 hours to yield of 1250 g of polyphosphoric acid, containing 80% of P$_2$O$_5$.

Method A (Intermediate Compounds)

4-(6-Bromo-pyridazin-3-yl)-1,4-diazabicyclo[3.2.2] nonane fumaric acid salt

A mixture of 3,6-dibromo-pyridazine (3.77 g; 15.85 mmol) 1,4-diazabicyclo[3.2.2]-nonane (2.00 g; 15.85 mmol) and aqueous sodium hydroxide (10 ml; 4M) was stirred at 100° C. for 30 minutes. The mixture was extracted with dichloromethane (3×20 ml). Chromatography on silica gel with dichloromethane, 10% methanol and 1% aqueous ammonia as solvent gave the title compound as an oil. Yield 0.88 g (20%). The corresponding salt was obtained by addition of a diethyl ether and methanol mixture (9:1) saturated with fumaric acid. Mp. 164.6-168.9° C.

4-(6-Chloro-pyridazin-3-yl)-1,4-diazabicyclo[3.2.2] nonane free base

The title compound was prepared according to Method A. Mp. 127.0-128.5° C.

Method B 4-(6-Phenylethynyl-pyridazin-3-yl)-1,4-diaza-bicyclo[3.2.2]nonane fumaric acid salt (Compound B1)

A mixture of 4-(6-bromo-pyridazin-3-yl)-1,4-diazabicyclo[3.2.2]nonane (1.0 g; 3.5 mmol), phenylacetylene (0.77 ml; 7.1 mmol), ethyldiisopropylamine (0.61 ml; 3.5 mmol), palladacycle (66 mg; 0.70 mmol) and dioxane (10 ml) was stirred at 100° C. for 15 hours. Aqueous sodium hydroxide (10 ml; 4M) was added. The mixture was extracted with dichloromethane (3×20 ml). Chromatography on silica gel with dichloromethane, 10% methanol and 1% aqueous ammonia as solvent gave the title compound as an oil. Yield 0.12 g (11%). The corresponding salt was obtained by addition of a diethyl ether and methanol mixture (9:1) saturated with fumaric acid. Mp. 196.7-197.9° C.

4-[6-(4-Amino-phenylethynyl)-pyridazin-3-yl]-1,4-diaza-bicyclo[3.2.2]nonane free base (Compound B2)

The title compound was prepared according to Method B. Mp. 181.7-183.4° C.

4-[6-(3-Fluoro-phenylethynyl)-pyridazin-3-yl]-1,4-diaza-bicyclo[3.2.2]nonane fumaric acid salt (Compound B3)

The title compound was prepared according to Method B. Mp. 173.5-175.0° C.

4-[6-(4-Methoxy-phenylethynyl)-pyridazin-3-yl]-1,4-diaza-bicyclo[3.2.2]nonane fumaric acid salt (Compound B4)

The title compound was prepared according to Method B. Mp. 208-209° C.

4-[6-(3-Pyridinlethynyl)-pyridazin-3-yl]-1,4-diaza-bicyclo[3.2.2]nonane fumaric acid salt (Compound B5)

The title compound was prepared according to Method B. Mp. 177.8-181.2° C.

Method C

4-(6-Phenylsulfanyl-pyridazin-3-yl)-1,4-diaza-bicyclo[3.2.2]nonane fumaric acid salt (Compound C1)

A mixture of 4-(6-chloro-pyridazin-3-yl)-1,4-diazabicyclo[3.2.2]nonane (0.27 g; 1.1 mmol) thiophenol (0.96 g; 8.4 mmol), caesium carbonate (369 mg; 1.1 mmol) and DMF (1 ml) was stirred at 125° C. for 15 hours. Aqueous sodium hydroxide (5 ml; 4M) was added. The mixture was extracted with dichloromethane (3×5 ml). Chromatography on silica gel with dichloromethane, 10% methanol and 1% aqueous ammonia as solvent gave the title compound as an oil. Yield 0.32 g (93%). The corresponding salt was obtained by addition of a diethyl ether and methanol mixture (9:1) saturated with fumaric acid. Mp. 102.2° C.

4-(6-Phenylsulfinyl-pyridazin-3-yl)-1,4-diaza-bicyclo[3.2.2]nonane fumaric acid salt (Compound C2)

The title compound was prepared from 4-(6-phenylsulfanyl-pyridazin-3-yl)-1,4-diaza-bicyclo[3.2.2]-nonane by oxidation with MCPBA in chloroform, followed reduction using PPh$_3$ in dioxane at reflux. Mp. 162° C.

4-(6-Phenoxy-pyridazin-3-yl)-1,4-diaza-bicyclo[3.2.2]nonane fumaric acid salt (Compound C3)

The title compound was prepared according to Method C, using NaH as base, palladacycle (5%) and copper (5 eq.) at 160° C. for 10 days. Mp. 146-156° C.

Method D

4-(5-Benzylsulfanyl-[1.3.4]-thiadiazol-3-yl)-1,4-diaza-bicyclo[3.2.2]nonane fumaric acid salt (Compound D1)

A mixture of 1,4-diazabicyclo[3.2.2]nonane (1.0 g; 7.9 mmol), 2,5-bis-benzylsulfany[1.3.4]thiadiazole and ethyldiisopropylamine (2.8 ml; 15.8 mmol) was stirred at 110° C. for 15 hours. Mp. 138.1-139.2° C.

Method E

1-[4-(1,4-Diaza-bicyclo[3.2.2]non-4-yl)-phenyl]-3-phenyl-urea free base (Compound E1)

A mixture of 4-(1,4-diaza-bicyclo[3.2.2]non-4-yl)-phenylamine (0.43 g, 2.0 mmol), phenylisocyanate (0.29 ml, 2.5 mmol) and methanol (60 ml) was stirred at room temperature for hours. The mixture was evaporated and diethylether (30 ml) was added, the precipitate was filtered. The product was isolated. Yield 0.23 g (34%). Mp. 145° C. (dec).

4-(4-Nitro-phenyl)-1,4-diaza-bicyclo[3.2.2]nonane hydrofluoric acid salt (Intermediate compound)

A mixture of 1,4-diazabicyclo[3.2.2]nonane (20.2 g, 160 mmol), 1-fluoro-4-nitrobenzene (17.5 ml, 163.3 mmol) and ethylene glycol diethyl ether (160 ml) was stirred at 135° C. for 18 hours. The mixture was cooled to room-temperature and diethyl ether (100 ml) was added. The mixture was filtered and the product was isolated by filtration. Yield 24.8 g (58%). Mp. 122-129° C.

4-(5-Nitro-pyridin-2-yl)-1,4-diaza-bicyclo[3.2.2]nonane (Intermediate compound)

1,4-diazabicyclo[3.2.2]nonane (6.3 g, 50 mmol) was added to a mixture of 2-chloro-nitropyridine (11.9, 75 mmol), and dioxane (250 ml) at 0° C. The reaction mixture was allowed to reach room-temperature. Water (100 ml) was added. The mixture was extracted with dichloromethane (3×50 ml). Chromatography on silica gel with dichloromethane and 10% methanol as solvent gave the title compound as an oil. Yield 8.1 g (65%). Mp. 143-146° C.

Method F

4-(1,4-Diaza-bicyclo[3.2.2]non-4-yl)-phenylamine (Intermediate compound)

A mixture of 4-(4-nitro-phenyl)-1,4-diaza-bicyclo[3.2.2]nonane (0.50 g, 2.0 mmol), palladium on carbon (100 mg, 10%) and methanol (60 ml) was stirred for 15 minutes under hydrogen (130 ml of hydrogen was consumed). The crude mixture was filtered through celite and the product was isolated as an oil in quantitative yield.

2-Amino-N-[4-(1,4-diaza-bicyclo[3.2.2]non-4-yl)-phenyl]-benzamide hydrochloric acid salt (Compound F1)

Was prepared according to Method F from N-[4-(1,4-diaza-bicyclo[3.2.2]non-4-yl)-phenyl]-2-nitro-benzamide. Mp. 238° C. (decomp.).

3-Amino-N-[4-(1,4-diaza-bicyclo[3.2.2]non-4-yl)-phenyl]-benzamide hydrochloric acid salt (Compound F2)

Was prepared according to Method F from N-[4-(1,4-diaza-bicyclo[3.2.2]non-4-yl)-phenyl]-3-nitro-benzamide. Mp. >250° C. (decomp.).

4-Amino-N-[4-(1,4-diaza-bicyclo[3.2.2]non-4-yl)-phenyl]-benzamide hydrochloric acid salt (Compound F3)

Was prepared according to Method F from N-[4-(1,4-diaza-bicyclo[3.2.2]non-4-yl)-phenyl]-4-nitro-benzamide. Mp. >250° C. (decomp.).

4-Amino-N-[6-(1,4-diaza-bicyclo[3.2.2]non-4-yl)-pyridin-3-yl]-benzamide hydrochloric acid salt (Compound F4)

Was prepared according to Method F from N-[6-(1,4-diaza-bicyclo[3.2.2]non-4-yl)-pyridin-3-yl]-4-nitro-benzamide. Mp. >272° C. (decomp.).

3-Amino-N-[6-(1,4-diaza-bicyclo[3.2.2]non-4-yl)-pyridin-3-yl]-benzamide hydrochloric acid salt (Compound F5)

Was prepared according to Method F from N-[6-(1,4-diaza-bicyclo[3.2.2]non-4-yl)-pyridin-3-yl]-3-nitro-benzamide. Mp. >244° C. (decomp.).

6-(1,4-Diaza-bicyclo[3.2.2]non-4-yl)-pyridin-3-ylamine (Intermediate compound)

Was prepared according to Method F.

4-Amino-N-[4-(1,4-diaza-bicyclo[3.2.2]non-4-yl)-phenyl]-benzenesulfonamide hydrochloric acid (Compound F6)

Was prepared according to Method F from N-[4-(1,4-Diaza-bicyclo[3.2.2]non-4-yl)-phenyl]-4-nitro-benzenesulfonamide. Mp. >265° C.

Method G

N-[4-(1,4-Diaza-bicyclo[3.2.2]non-4-yl)-phenyl]-benzamide hydrochloric acid salt (Compound G1)

4-(1,4-Diaza-bicyclo[3.2.2]non-4-yl)-phenylamine (0.76 g, 3.5 mmol), benzoyl chloride (0.41 g, 3.5 mmol) and dichloromethane (33 ml) was stirred at room temperature for 17 hours. The mixture was evaporated and triturated with diethyl ether (50 ml). The crystals were recrystallised from methanol (40 ml). The hydrochloric acid salt was isolated. Yield 0.54 g (44%). Mp. 260° C. (decomp.).

N-[4-(1,4-Diaza-bicyclo[3.2.2]non-4-yl)-phenyl]-2-nitro-benzamide hydrochloric acid salt (Compound G2)

Was prepared by Method G from 4-(1,4-Diaza-bicyclo[3.2.2]non-4-yl)-phenylamine and 2-nitrobenzoyl chloride. Mp. >280° C.

N-[4-(1,4-Diaza-bicyclo[3.2.2]non-4-yl)-phenyl]-3-nitro-benzamide hydrochloric acid salt (Compound G3)

Was prepared by Method G from 4-(1,4-diaza-bicyclo[3.2.2]non-4-yl)-phenylamine and 3-nitrobenzoyl chloride. Mp. >280° C.

N-[4-(1,4-Diaza-bicyclo[3.2.2]non-4-yl)-phenyl]-4-nitro-benzamide hydrochloric acid salt (Compound G4)

Was prepared by Method G from 4-(1,4-diaza-bicyclo[3.2.2]non-4-yl)-phenylamine and 4-nitrobenzoyl chloride. Mp. >280° C.

N-[4-(1,4-Diaza-bicyclo[3.2.2]non-4-yl)-phenyl]-3-methoxy-benzamide hydrochloric acid salt (Compound G5)

Was prepared by Method G from 4-(1,4-diaza-bicyclo[3.2.2]non-4-yl)-phenylamine and 3-methoxybenzoyl chloride. Mp. 260° C.

N-[4-(1,4-Diaza-bicyclo[3.2.2]non-4-yl)-phenyl]-benzenesulfonamide free base (Compound G6)

Was prepared by Method G from 4-(1,4-diaza-bicyclo[3.2.2]non-4-yl)-phenylamine and phenylsulfonyl chloride. Mp. 267° C.

N-[4-(1,4-Diaza-bicyclo[3.2.2]non-4-yl)-phenyl]-4-methoxy-benzamide hydrochloric acid salt (Compound G7)

Was prepared by Method G from 4-(1,4-diaza-bicyclo[3.2.2]non-4-yl)-phenylamine and 4-methoxybenzoyl chloride. Mp. >275° C.

N-[4-(1,4-Diaza-bicyclo[3.2.2]non-4-yl)-phenyl]-3-cyano-benzamide hydrochloric acid salt (Compound G8)

Was prepared by Method G from 4-(1,4-diaza-bicyclo[3.2.2]non-4-yl)-phenylamine and 3-cyanobenzoyl chloride. Mp. 250° C. (decomp.).

N-[4-(1,4-Diaza-bicyclo[3.2.2]non-4-yl)-phenyl]-4-cyano-benzamide hydrochloric acid salt (Compound G9)

Was prepared by Method G from 4-(1,4-diaza-bicyclo[3.2.2]non-4-yl)-phenylamine and 4-cyanobenzoyl chloride. Mp. 250° C. (decomp.).

N-[4-(1,4-Diaza-bicyclo[3.2.2]non-4-yl)-phenyl]-3-fluoro-benzamide hydrochloric acid salt (Compound G10)

Was prepared by Method G from 4-(1,4-diaza-bicyclo[3.2.2]non-4-yl)-phenylamine and 3-fluorobenzoyl chloride. Mp. >270° C. (decomp.).

N-[4-(1,4-Diaza-bicyclo[3.2.2]non-4-yl)-phenyl]-4-fluoro-benzamide hydrochloric acid salt (Compound G11)

Was prepared by Method G from 4-(1,4-diaza-bicyclo[3.2.2]non-4-yl)-phenylamine and 4-fluorobenzoyl chloride. Mp. >270° C. (decomp.).

N-[4-(1,4-Diaza-bicyclo[3.2.2]non-4-yl)-phenyl]-2-fluoro-benzamide hydrochloric acid salt (Compound G12)

Was prepared by Method G from 4-(1,4-diaza-bicyclo[3.2.2]non-4-yl)-phenylamine and 2-fluorobenzoyl chloride. Mp. >268° C. (decomp.).

N-[6-(1,4-Diaza-bicyclo[3.2.2]non-4-yl)-pyridin-3-yl]-benzamide hydrochloric acid salt (Compound G13)

Was prepared according to Method G from 6-(1,4-diaza-bicyclo[3.2.2]non-4-yl)-pyridin-3-ylamine. Mp. 285° C. (decomp.).

1-[6-(1,4-Diaza-bicyclo[3.2.2]non-4-yl)-pyridin-3-yl]-3-(2-nitro-phenyl)-urea-1-N-oxide (Compound G14)

Was prepared according to Method G from 6-(1,4-diaza-bicyclo[3.2.2]non-4-yl)-pyridin-3-ylamine and 2-nitrophenylisocyanate. Mp. 139° C. (decomp.).

1-[6-(1,4-Diaza-bicyclo[3.2.2]non-4-yl)-pyridin-3-yl]-3-phenyl-urea hydrochloric acid salt (Compound G15)

Was prepared according to Method G from 6-(1,4-diaza-bicyclo[3.2.2]non-4-yl)-pyridin-3-ylamine and phenylisocyanate. Mp. 235° C. (decomp.).

N-[6-(1,4-Diaza-bicyclo[3.2.2]non-4-yl)-pyridin-3-yl]-4-nitro-benzamide hydrochloric acid salt (Compound G16)

Was prepared according to Method G from 6-(1,4-diaza-bicyclo[3.2.2]non-4-yl)-pyridin-3-ylamine and 4-nitrobenzoyl chloride. Mp. >310° C. (decomp.).

N-[6-(1,4-Diaza-bicyclo[3.2.2]non-4-yl)-pyridin-3-yl]-3-nitro-benzamide hydrochloric acid salt (Compound G17)

Was prepared according to Method G from 6-(1,4-diaza-bicyclo[3.2.2]non-4-yl)-pyridin-3-ylamine and 3-nitrobenzoyl chloride. Mp. >280° C. (decomp.).

N-[4-(1,4-Diaza-bicyclo[3.2.2]non-4-yl)-phenyl]-4-nitro-benzenesulfonamide hydrochloric acid salt (Compound G18)

Was prepared according to Method G from 6-(1,4-diaza-bicyclo[3.2.2]non-4-yl)-pyridin-3-ylamine and 4-nitrophenylsulfonyl chloride. Mp. >300° C. (decomp.).

N-[6-(1,4-Diaza-bicyclo[3.2.2]non-4-yl)-pyridin-3-yl]-3-methoxy-benzamide hydrochloric acid salt (Compound G19)

Was prepared according to Method G from 6-(1,4-diaza-bicyclo[3.2.2]non-4-yl)-pyridin-3-ylamine and 3-methoxy-benzoyl chloride. Mp. >265° C. (decomp.).

N-[6-(1,4-Diaza-bicyclo[3.2.2]non-4-yl)-pyridin-3-yl]-3-cyano-benzamide hydrochloric acid salt (Compound G20)

Was prepared according to Method G from 6-(1,4-diaza-bicyclo[3.2.2]non-4-yl)-pyridin-3-ylamine and 3-cyanobenzoyl chloride. Mp. >265° C. (decomp.).

N-[6-(1,4-Diaza-bicyclo[3.2.2]non-4-yl)-pyridin-3-yl]-4-cyano-benzamide hydrochloric acid salt (Compound G21)

Was prepared according to Method G from 6-(1,4-diaza-bicyclo[3.2.2]non-4-yl)-pyridin-3-ylamine and 4-cyanobenzoyl chloride. Mp. >300° C.

Method H

2-Acetylamino-N-[4-(1,4-diaza-bicyclo[3.2.2]non-4-yl)-phenyl]-benzamide free base (Compound H1)

Acetic acid (2 ml) was added to a mixture of 2-Amino-N-[4-(1,4-diaza-bicyclo[3.2.2]non-4-yl)-phenyl]-benzamide hydrochloric acid salt (365 mg, 1.1 mmol), sodium acetate (4.4 g, 54.2 mmol) and water (100 ml) at 0° C. The mixture was made alkaline by adding saturated sodium bicarbonate (20 ml). The mixture was extracted with ethyl acetate (3×50 ml). The product was isolated. Yield 95 mg (23%). Mp. 191° C.

3-Acetylamino-N-[4-(1,4-diaza-bicyclo[3.2.2]non-4-yl)-phenyl]-benzamide free base (Compound H 2)

Was prepared according to Method H. Mp. 184-187° C.

4-Acetylamino-N-[4-(1,4-diaza-bicyclo[3.2.2]non-4-yl)-phenyl]-benzamide free base (Compound H3)

Was prepared according to Method H. Mp. >240° C.

4-Acetylamino-N-[6-(1,4-diaza-bicyclo[3.2.2]non-4-yl)-pyridin-3-yl]-benzamide free base (Compound H4)

Was prepared according to Method H. Mp. 255° C. (decomp.).

3-Acetylamino-N-[6-(1,4-diaza-bicyclo[3.2.2]non-4-yl)-pyridin-3-yl]-benzamide free base (Compound H5)

Was prepared according to Method H. Mp. 60° C.

Example 2

In Vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $α_7$ subunit isoform found in brain and the at isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C.

Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | $IC_{50}$ (μM) |
| B1 | 0.060 |
| B4 | 0.18 |
| B5 | 0.15 |
| C1 | 0.60 |

The invention claimed is:

1. A diazabicyclic aryl derivative represented by Formula I

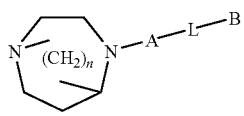

(I)

or an enantiomer or pharmaceutically acceptable salt thereof, wherein n is 2;

A represents phenyl, thiadiazolyl, pyridyl or pyridazinyl;

B represents a phenyl or pyridyl group, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —C≡C—, —NHCO— or —NH($SO_2$)—.

2. The diazabicyclic aryl derivative of claim 1, wherein

A represents phenyl;

B represents a phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —C≡C—, —NHCO— or —NH($SO_2$)—.

3. The diazabicyclic aryl derivative of claim 2, which is

N-[4-(1,4-Diaza-bicyclo[3.2.2]non-4-yl)-phenyl]-benzamide;

N-[4-(1,4-Diaza-bicyclo[3.2.2]non-4-yl)-phenyl]-2-nitrobenzamide;

N-[4-(1,4-Diaza-bicyclo[3.2.2]non-4-yl)-phenyl]-3-nitrobenzamide;

N-[4-(1,4-Diaza-bicyclo[3.2.2]non-4-yl)-phenyl]-4-nitrobenzamide;

2-Amino-N-[4-(1,4-diaza-bicyclo[3.2.2]non-4-yl)-phenyl]-benzamide;

3-Amino-N-[4-(1,4-diaza-bicyclo[3.2.2]non-4-yl)-phenyl]-benzamide;

4-Amino-N-[4-(1,4-diaza-bicyclo[3.2.2]non-4-yl)-phenyl]-benzamide;

2-Acetylamino-N-[4-(1,4-diaza-bicyclo[3.2.2]non-4-yl)-phenyl]-benzamide;

3-Acetylamino-N-[4-(1,4-diaza-bicyclo[3.2.2]non-4-yl)-phenyl]-benzamide;

4-Acetylamino-N-[4-(1,4-diaza-bicyclo[3.2.2]non-4-yl)-phenyl]-benzamide;

N-[4-(1,4-Diaza-bicyclo[3.2.2]non-4-yl)-phenyl]-3-methoxy-benzamide;

N-[4-(1,4-Diaza-bicyclo[3.2.2]non-4-yl)-phenyl]-benzenesulfonamide;

N-[4-(1,4-Diaza-bicyclo[3.2.2]non-4-yl)-phenyl]-4-methoxy-benzamide;

N-[4-(1,4-Diaza-bicyclo[3.2.2]non-4-yl)-phenyl]-3-cyano-benzamide;

N-[4-(1,4-Diaza-bicyclo[3.2.2]non-4-yl)-phenyl]-4-cyano-benzamide;

N-[4-(1,4-Diaza-bicyclo[3.2.2]non-4-yl)-phenyl]-3-fluoro-benzamide;

N-[4-(1,4-Diaza-bicyclo[3.2.2]non-4-yl)-phenyl]-4-fluoro-benzamide;

N-[4-(1,4-Diaza-bicyclo[3.2.2]non-4-yl)-phenyl]-2-fluoro-benzamide;

N-[4-(1,4-Diaza-bicyclo[3.2.2]non-4-yl)-phenyl]-4-nitro-benzenesulfonamide; or

4-Amino-N-[4-(1,4-diaza-bicyclo[3.2.2]non-4-yl)-phenyl]-benzenesulfonamide;

or an enantiomer or pharmaceutically acceptable salt thereof.

4. The diazabicyclic aryl derivative of claim 1, wherein

A represents thiadiazolyl, pyridyl or pyridazinyl;

B represents phenyl or pyridyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —C≡C—, —NHCO— or —NH($SO_2$)—.

5. The diazabicyclic aryl derivative of claim 4, wherein A represents thiadiazolyl.

6. The diazabicyclic aryl derivative of claim 4, wherein A represents pyridyl or pyridazinyl.

7. The diazabicyclic aryl derivative of claim 6, which is 4-(6-Phenylethynyl-pyridazin-3-yl)-1,4-diaza-bicyclo[3.2.2]nonane;

4-[6-(4-Amino-phenylethynyl)-pyridazin-3-yl]-1,4-diaza-bicyclo[3.2.2]nonane;

4-[6-(3-Fluoro-phenylethynyl)-pyridazin-3-yl]-1,4-diaza-bicyclo[3.2.2]nonane;

4-[6-(4-Methoxy-phenylethynyl)-pyridazin-3-yl]-1,4-diaza-bicyclo[3.2.2]nonane;

4-[6-(3-Pyridinylethynyl)-pridazin-3-yl]-1,4-diaza-bicyclo[3.2.2]nonane;

4-(6-Phenylsulfinyl-pyridazin-3-yl)-1,4-diaza-bicyclo[3.2.2]nonane;

N-[6-(1,4-Diaza-bicyclo[3.2.2]non-4-yl)-pyridin-3-yl]-benzamide;

N-[6-(1,4-Diaza-bicyclo[3.2.2]non-4-yl)-pyridin-3-yl]-4-nitro-benzamide;

N-[6-(1,4-Diaza-bicyclo[3.2.2]non-4-yl)-pyridin-3-yl]-3-nitro-benzamide;

4-Amino-N-[6-(1,4-diaza-bicyclo[3.2.2]non-4-yl)-pyridin-3-yl]-benzamide;

3-Amino-N-[6-(1,4-diaza-bicyclo[3.2.2]non-4-yl)-pyridin-3-yl]-benzamide;

4-Acetylamino-N-[6-(1,4-diaza-bicyclo[3.2.2]non-4-yl)-pyridin-3-yl]-benzamide;

3-Acetylamino-N-[6-(1,4-diaza-bicyclo[3.2.2]non-4-yl)-pyridin-3-yl]-benzamide;

N-[6-(1,4-Diaza-bicyclo[3.2.2]non-4-yl)-pyridin-3-yl]-3-methoxy-benzamide;

N-[6-(1,4-Diaza-bicyclo[3.2.2]non-4-yl)-pyridin-3-yl]-3-cyano-benzamide; or

N-[6-(1,4-Diaza-bicyclo[3.2.2]non-4-yl)-pyridin-3-yl]-4-cyano-benzamide;

or an enantiomers or a mixture of its enantiomers, or a pharmaceutically acceptable salt thereof.

8. The diazabicyclic aryl derivative of claim 6, which is;

4-[6-(4-Amino-phenylethynyl)-pyridazin-3-yl]-1,4-diaza-bicyclo[3.2.2]nonane;

or an enantiomers or a mixture of its enantiomers, or a pharmaceutically acceptable salt thereof.

9. A pharmaceutical composition comprising a therapeutically effective amount of a diazabicyclic aryl derivative of claim 1, or a pharmaceutically-acceptable addition salt thereof, together with at least one pharmaceutically-acceptable carrier or diluent.

* * * * *